(12) United States Patent
Heaton et al.

(10) Patent No.: US 8,808,763 B2
(45) Date of Patent: *Aug. 19, 2014

(54) METHODS FOR IMPROVING SLEEP EFFICIENCY IN HEALTHY HUMAN BEINGS

(71) Applicant: Quality IP Holdings, Inc., Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,097

(22) Filed: Sep. 19, 2012

(65) Prior Publication Data

US 2014/0079822 A1  Mar. 20, 2014

(51) Int. Cl.
| | |
|---|---|
| A61K 36/55 | (2006.01) |
| A61K 36/00 | (2006.01) |
| A61K 47/00 | (2006.01) |
| A61K 9/14 | (2006.01) |
| A61K 9/00 | (2006.01) |
| A61K 31/198 | (2006.01) |
| A61K 36/538 | (2006.01) |
| A61K 31/4015 | (2006.01) |

(52) U.S. Cl.
CPC ............ *A61K 36/538* (2013.01); *A61K 31/198* (2013.01); *A61K 31/4015* (2013.01)
USPC ........... 424/745; 424/725; 424/774; 424/439; 424/489; 424/400

(58) Field of Classification Search
None
See application file for complete search history.

(56) References Cited

U.S. PATENT DOCUMENTS 6,071,926 A * 6/2000 Van Cauter et al. .......... 514/278

OTHER PUBLICATIONS

Pavel et al. (2003) Horm. Metab. Res. 35: 114-119.*
Website document entitled: "Growth Hormone: Amino Acids as GH secretagogues" (available at http://www.vrp.com/amino-acids/growth-hormone-amino-acids-as-gh-secretagogues-a-review-of-the-literature?utm_source=RSStwitterfeed&utm_medium=twitter) Dowloaded from website: Apr. 8, 2013.*
Fung, et al. (2002) J. Clin. Pharmacol. 42: 30-36.*
Reid et al. (1994) J. Clin. Invest. 94: 2468-2474.*
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.
Albert et al.; Low-Dose Recombinant Human Growth Hormone as Adjuvant Therapy of Lifestyle Modiifcations in the Management of Obesity; Journal of Clinical Endocrinology & Metabolism 89(2) 695-704; 2004.
Bernardi et al.; Somatotropic axis and body weight in pre-menopausal and post-menopausal women: evidence fora neuroendocrine derangement, in absence of changes of insulin-like growth factor binding protein concentrations; Human Reproduction vol. 12, No. 2 pp. 279-287, 1998.
Bidlingmaier et al.; Growth Hormone; Handbook of Experimental Pharmacology 195; 2010; pp. 187-200.
Bjorntorp, et al.; Hypothalamic Origin of the Metabolic Syndrome X; Annals New York Academy of Sciences, pp. 297-307; 1999.
Bjorntorp, P.; Do Stress reactions cause abdominal obesity and comorbidities?; The International Association for the Study of Obesity, Obesity reviews; 2 73-85; 2001.
Bjorntorp, P.; The regulation of adipose tissue distribution in humans; International Journal of Obesity (1996) 20, 191-302.
Blackman et al.; Growth Hormone and Sex Steroid Administration in Healthy Aged Women and Men a Randomized Controlled Trial; JAMA, Nov. 12, 2002—vol. 288, No. 18; pp. 2282-2292.
Bredella, et al.; Peak Growth Hormone-Releasing Hormone-Arginine-Stimulated Growth Hormone iS Inversely Associated with Intramyocellular and Intrahepatic Lipid Contentin Premenopausal Women with Obesity; J. Clin Endocrinol Metab. Oct. 2009; 94(10): 3995-4002.
Carli et al.; Changes in the exercise-induced hormone response to branched chain amino acid administration; Eru. J. Apl. Physiology (1992) 64:272-277.
Chromiak et al.; Use of Amino Acids as Growth Hormone-Releasing Agents by Athletes; Nutrition 18:657-661, 2002.
Corpas et al.; Human Growth Hormone and Human Aging; Endocrine Reviews, vol. 14, No. 1; 1993; pp. 20-39.
Corpas et al.; Oral Arginine-Lysine Does not Increase Growth Hormone or Insulin-like Growth Factor-I in Old Men; Journal of Gerontology: 1993, vol. 48, No. 4, M128-M133.
Ding et al.; Novel serum protein bio markers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate d'ornithine sur le taux plamatique de l'hormone de croissane (HGH); Annels D'Endocrinologie; pp. 526-528; 1972.
Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.

(Continued)

*Primary Examiner* — Chris R Tate
*Assistant Examiner* — Russell Fiebig
(74) *Attorney, Agent, or Firm* — TraskBritt

(57) ABSTRACT

Embodiments of the invention generally relate to methods and supplements for improving sleep efficiency in human beings.

17 Claims, 1 Drawing Sheet

(56) References Cited

OTHER PUBLICATIONS

Hersch et al.; Growth hormone (GH)-releasing hormone and GH secretagogues in normal aging: Fountain of Youth or Pool of Tantalus?; Clinical Interventions in Aging 2008:3(1) 121-129.

Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088, 1991.

Isidori et al.; A Study of growth hormone release in man after oral administration of amino acids; Current Medical Research and Opinion; vol. 7, No. 7, 1981; pp. 475-481.

Karlsson et al.; Effects of growth hormone treatment on the leptin system and on energy expenditure in abdominally obese men; European Journal of Endocrinology (1998) 138 408-414.

Kraemer et al.; Chronic Resistance training in women potentiates growth hormone in vivo bioactivity: characterization of molecular mass variants; Am. J. Physiol Endocrinol Metab 291: E1177-E1187, 2006.

Lambert et al.; Failure of Commercial Oral Amino Acid Supplements to Increase Serum Growth Hormone Concentrations in Male Body-Builders; International Journal of Sport Nutrition, 1993, 3, 298-305.

Legakis et al.; Human Galanin Secretion is Increased Upon Normal Exercise Test in Middle-Age Individuals; Endocrine Research 26(3), 357-365 (2000).

Maccario et al.; Relationships between IFG-I and age, gender, body mass, fat distribution, metabolic and hormonal variables in obese patients; International Journal of Obesity (1999) 23, 612-618.

Makimura et al.; The relationship between reduced testosterone, stimulated growth hormone secretion and increased carotid inima-media thickness in obese men; Clin Endocrinol (Oxf). Nov. 2010; 73(5): 622-629.

Menagh et al.; Growth Hormone Regulates the Balance Between Bone Formation and Bone Marrow Adiposity; JBMR, vol. 25, No. 4, Apr. 2010, pp. 757-768.

Merimee et al.; Arginine-Initiated Release of Human Growth Hormone; The New England Journal of Medicine; Jun. 26, 1969; pp. 1434-1438.

Nindl et al.; Growth hormone pulsatility profile characteristics followingacute heavy resistance exercise; J. Appl Physiol 91: 163-172, 2001.

O'Connor et al.; Interrelationships of Spontaneous Growth Hormone Axis Activity, Body Fat, and Serum Lipids in Healthy Elderly Women and Men; Metabolism, vol. 48, No. 11 Nov. 1999: pp. 1424-1431.

Papadakis et al.; Effect of growth hormone replacement on wound healing in healthy older men; Would Repair and Regeneration Oct.-Dec. 1996; pp. 421-425.

Papadakis et al.; Growth Hormone Replacement in Healthy Older Men Improves Body Composition but Not Functional Ability; Ann Intern Med. 1996; 124-: 708-716.

Pasquali et al.; Hormones and pathophysiology of obesity; Hormones and Obesity; 2001 pp. 9-20.

Pelsers et al.; Influence of Gender in Growth Hormone Status in Adults: Role of Urinary Growth Hormone; Clinical Chemistry 45, No. 3, 1999, pp. 443-444.

Perry, Horace M. III; The Endocrinology of Aging; Clinical Chemistry 45:8(B); 1369-1376 (1999).

Rubin et al.; New anabolic therapies in osteoporosis; Current Opinon in Reeumatology 2002, 14:433-440.

Rudman et al.; Effects of Human Growth Hormone in Men over 60 Years Old; The New England Journal of Medicine; vol. 323, Jul. 5, 1990; 6 pages.

Su et al.; Insulin-like growth factor 1 and hair growth; 1999 Dermatology OnlineJournal; 20 pages.

Suminski et al.; Acute Effect of Amino Acid Ingestion and Resistance Exercise on Plasma Growth Hormone Concentration in Young Men; International Journal of Sport Nutrition, 1997, 7, 48-60.

Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488, 2002.

Vance, Mary L.; Growth Hormone for the Elderly?; The New England Journal of Medicine; Jul. 5, 1990; pp. 52-54.

White et al.; Effects of an Oral Growth Hormone Secretagogue in Older Adults; J. Clin Endocrin Metab.; 2009; 29 pages.

Zouboulis et al.; Intrinsische Hautalterung; Eine kritische Bewertung der Rolle der Hormone; Hautarzt 2003 54: 825-832.

\* cited by examiner

Figure 1: Time to fall asleep
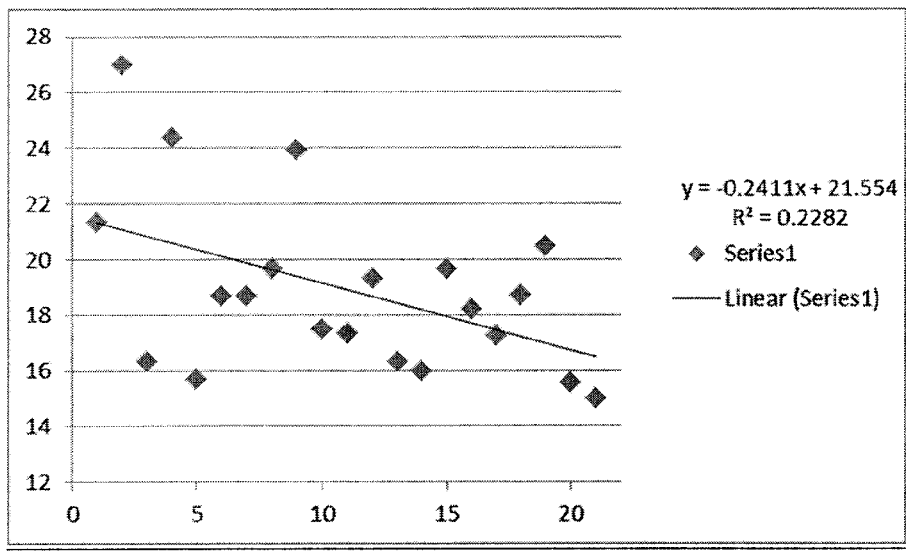
Figure 2: Time awake during sleep
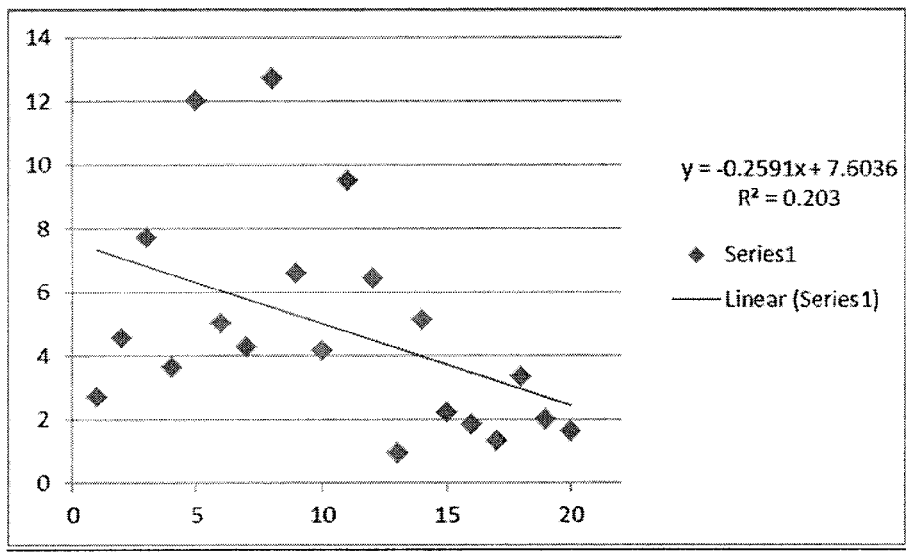

METHODS FOR IMPROVING SLEEP EFFICIENCY IN HEALTHY HUMAN BEINGS

TECHNICAL FIELD

Embodiments of the invention generally relate to methods and supplements for improving sleep efficiency in healthy humans.

BACKGROUND

A circadian rhythm is any biological process that displays an endogenous, entrainable oscillation of about 24 hours. These rhythms are driven by a circadian clock, and rhythms have been widely observed in plants, animals, fungi and cyanobacteria. The term circadian comes from the Latin circa, meaning "around" (or "approximately"), and diem or dies, meaning "day". The formal study of biological temporal rhythms, such as daily, tidal, weekly, seasonal, and annual rhythms, is called chronobiology. Although circadian rhythms are endogenous ("built-in", self-sustained), they are adjusted (entrained) to the local environment by external cues called zeitgebers, commonly the most important of which is daylight.

Circadian rhythmicity is present in the sleeping and feeding patterns of animals, including human beings. There are also clear patterns of core body temperature, brain wave activity, hormone production, cell regeneration and other biological activities. In addition, photoperiodism, the physiological reaction of organisms to the length of day or night, is vital to both plants and animals, and the circadian system plays a role in the measurement and interpretation of day length. The primary circadian "clock" in mammals is located in the suprachiasmatic nucleus (or nuclei) (SCN), a pair of distinct groups of cells located in the hypothalamus. The SCN receives information about illumination through the eyes. The retina of the eye contains "classical" photoreceptors ("rods" and "cones"), which are used for conventional vision. But the retina also contains specialized ganglion cells which are directly photosensitive, and project directly to the SCN where they help in the entrainment of this master circadian clock.

These cells contain the photopigment melanopsin and their signals follow a pathway called the retinohypothalamic tract, leading to the SCN. If cells from the SCN are removed and cultured, they maintain their own rhythm in the absence of external cues.

The SCN takes the information on the lengths of the day and night from the retina, interprets it, and passes it on to the pineal gland, a tiny structure shaped like a pine cone and located on the epithalamus. In response, the pineal secretes the hormone melatonin. Secretion of melatonin peaks at night and ebbs during the day and its presence provides information about night-length.

Several studies have indicated that pineal melatonin feeds back on SCN rhythmicity to modulate circadian patterns of activity and other processes. However, the nature and system-level significance of this feedback are unknown.

It would be desirable to provide a nutritional supplement for improving sleep efficiency in healthy humans.

BRIEF SUMMARY OF THE INVENTION

Described herein are nutritional supplement and method of using the same. The nutritional supplement includes an amino acid secretagogue composition, which, taken orally, stimulates the pituitary gland to release hGH.

Some embodiments include an oral nutritional supplement that comprises L-arginine, oxo-proline, and L-lysine.

A particular embodiment of the present disclosure relates to an oral nutritional supplement that includes the amino acids l-lysine, l-arginine, oxo-proline, and one of either cysteine or glutamine. The amino acids may be delivered as non-toxic salts thereof, effective complexes thereof, stable chelates thereof, active esters thereof, functional derivatives thereof, and mixtures thereof which are effective to increase hGH levels in the general population.

Another particular embodiment relates to an oral nutritional supplement that consists essentially of 1-lysine HCl, 1-arginine HCl, oxo-proline, N-acetyl-1-cysteine, 1-glutamine, and schizonepeta (aerial parts) powder.

Other embodiments are drawn to methods of increasing human growth hormone in humans that include orally administering the disclosed nutritional supplement to a healthy human being.

BRIEF DESCRIPTION OF THE FIGURES

FIG. 1 shows a linear regression analysis of time to fall asleep with continued use of the supplement over time; and FIG. 2 shows time awake during sleep over time with continued use of the supplement.

DETAILED DESCRIPTION OF THE INVENTION

The present invention relates to a nutritional supplement for use by a human being. The supplement of the present invention works as a dietary supplement by assisting the body's own ability to improve sleep efficiency naturally in a manner which is safe and effective, as well as being affordable.

A particular embodiment of the present disclosure relates to an oral nutritional supplement that includes 1-lysine, 1-arginine, oxo-proline, and one of either cysteine or glutamine. The supplement may additionally include both cysteine and glutamine and/or schizonepeta powder. In particular embodiments, a functional dosage includes the 1-arginine at a level between 0.1-6 mmol and the oxo-proline between 0.1-8 mmol, and/or the 1-lysine in an amount between 0.1-12 mmol. The cysteine and/or glutamine may be contained at a level between 0.001-6 mmol. In another particular embodiment, a functional dosage includes the 1-arginine at a level between 2.5-4.5 mmol and the oxo-proline between 4-6 mmol, and/or the 1-lysine in an amount between 7-9 mmol. The cysteine and/or glutamine may be contained at a level between 0.001-0.5 mmol. The cysteine can be n-acetyl L-cysteine and the glutamine may be 1-glutamine. The amino acids may be delivered as non-toxic salts thereof, effective complexes thereof, stable chelates thereof, active esters thereof, functional derivatives thereof, and mixtures thereof which are effective to increase hGH levels in the general population. The nutritional supplement may be present in an amount of 2.9 grams. The nutritional supplement may be in any acceptable and known oral formulation, such as powder, tablet, capsule, liquid, or wafer form.

Another particular embodiment relates to an oral nutritional supplement that consists essentially of 1-lysine HCl, 1-arginine HCl, oxo-proline, N-acetyl-1-cysteine, 1-glutamine, and schizonepeta (aerial parts) powder. In particular embodiments, a functional dosage includes the 1-arginine HCl at a level between 0.1-6 mmol and the oxo-proline between 0.1-8 mmol, and/or the 1-lysine HCl in an amount between 0.1-12 mmol. The n-acetyl L-cysteine and/or 1-glutamine may be contained at a level between 0.001-6 mmol. In another particular embodiment, a functional dosage includes the 1-arginine HCl at a level between 2.5-4.5 mmol and the oxo-proline between 4-6 mmol, and/or the 1-lysine HCl in an amount between 7-9 mmol. The n-acetyl L-cysteine and/or 1-glutamine may be contained at a level between 0.001-0.5 mmol. The nutritional supplement may be in any acceptable and known oral formulation, such as powder, tablet, capsule, liquid, or wafer form.

Other embodiments are drawn to methods of increasing human growth hormone in humans that include orally administering the disclosed nutritional supplement to a healthy human being. As used herein, "healthy human being" means a human being without any physiological deficiency in hGH independent of age. Particular embodiments of the invention relate to oral administration of the disclosed nutritional supplement to a human that is at least 30 years old. The nutritional supplement may be administered from one to three times daily or, alternatively, may be administered every other day, or may be administered once a week. In particular embodiments, the nutritional supplement may be administered on an empty stomach.

In accordance with the "consist essentially of" and "consisting essentially of" language, the nutritional supplement of the third embodiments is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement of the present invention may be prepared in accordance with any method known to one of ordinary skill in the art. Alternatively, each ingredient may be obtained in a fully prepared from a commercially available source.

The nutritional supplement of the present invention may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement of the present invention may be ingested on a regular basis, such as a daily or weekly intake at a dosage tailored to an individual's needs; i.e., the nutritional supplement is to be taken regularly as multiples (1×, 2×, etc.) of the structural units (pills, tablets, capsules, liquid dose, etc.) in accordance with the needs of the individual. For example, a senior citizen leading a sedentary life may need higher daily doses than does a young person engaged in regular strenuous exercise (e.g., a weight lifter). Alternatively, the nutritional supplement of the present invention may be ingested on an as-needed basis at a dosage tailored to the individual's needs. Medical or nutritional counseling may be beneficial for arriving at a desirable or optimal dosage tailored to the individual's needs.

The combination of types of amino acids, mass ranges, and specific formulations have been selected to be synergistically balanced and of adequate quantity to achieve the desired physiological effect, namely, improving sleep efficiency. Improper combinations of the amino acids may be ineffective. The component amino acids are synergistic in the sense that several of them when combined together, synergistically improve sleep efficiency. The combination was also chosen to reduce or inhibit chemical combination or reaction between the amino acids.

EXAMPLES

A double-blind clinical study involved 15 healthy subjects [10 males, 5 females; mean age=33±7 years]. Each subject completed a baseline Epworth Sleepiness Scale self-report questionnaire and a standardized assay of usual sleep habits. All subjects were deemed to have average sleep parameters within a normal range.

The subjects were then provided a three week supply of a novel supplement SeroVital (2.9 g/dose blend of 1-lysine HCl, 1-arginine HCl, oxo-proline, N-acetyl-1-cysteine, 1-glutamine, and schizonepeta (aerial parts) powder). The novel SeroVital blend has been shown previously to increase serum human growth hormone hGH levels by 8 times (equivalent to 682%) 120 minutes after a single dose in healthy male and female volunteers. Because night-time onset of hGH has been directly correlated to sleep efficiency, we investigated sleep patterns with continued use of the supplement when taken on an empty stomach, two hours after dinner prior to bedtime, every night for three weeks. On each trial day, subjects reported 1) time went to bed; 2) time of final wakening; 3) estimated time to fall asleep; 4) time of awakening during sleep/length of time awake. Data was compiled by day for estimated time to fall asleep and length of time awake during sleep in order to assess sleep efficiency. Daily values for each measure were plotted as an average (±S.D.) among the subjects over the time course of the study, and a linear regression was tabulated to assess overall trends over time. All available data was included in the analysis.

Linear regression analysis showed that both estimated time to fall asleep (FIG. 1) and time awake during sleep (FIG. 2) tended to decrease over time with continued use of the supplement over the time course of the study. Time to fall asleep decreased with an average slope of −0.24 min/day, and time awake during sleep decreased by an average slope of −0.26 min/day. Overall, these results so a trend towards greater sleep efficiency by measurements of both time to fall asleep and time awake during sleep, both with a quantified average decrease of about 0.25 min/day over three weeks with regular nighttime use of the novel SeroVital supplement (when taken as directed, on an empty stomach, two hours after dinner prior to bedtime).

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method of improving sleep efficiency in a healthy human being in need thereof, comprising:
   providing a nutritional supplement composition in unit dosage form, wherein the unit dosage consists of:
      about 1 mmol L-arginine;
      about 1 mmol Oxo-proline;
      about 2 mmol L-lysine;
      about 1.5 µmol N-acetyl L-cysteine;
      about 2 µmol L-glutamine; and
   about 125 µg Schizonepta (aerial parts) powder; and
   orally administering an effective amount of the nutritional supplement composition to the human being.

2. The method of claim 1, where the effective amount of the nutritional supplement composition is 2.9 grams.

3. The method of claim 1, wherein the nutritional supplement composition is in powder, tablet, capsule, liquid or wafer form.

4. The method of claim 1, wherein orally administering the nutritional supplement composition to a healthy human being comprises orally administering the nutritional supplement composition to the human being from one to three times daily.

5. The method of claim 1, wherein orally administering the nutritional supplement composition to a healthy human being comprises orally administering the nutritional supplement composition to the human being once a week.

6. The method of claim 1, wherein orally administering the nutritional supplement composition to a healthy human being comprises orally administering the nutritional supplement composition to the human being on an empty stomach.

7. The method of claim 1, wherein the healthy human being is a female human being.

8. A method of improving sleep efficiency in a healthy human being in need thereof, comprising:
providing
a nutritional supplement composition in unit dosage form, wherein unit dosage form consists of:
0.86 mmol L-arginine;
1.32 mmol Oxo-proline;
2.05 mmol L-lysine;
1.53 µmol N-acetyl L-cysteine;
1.71 µmol L-glutamine; and
125 µg Schizonepta (aerial parts) powder and
orally administering an effective amount of the nutritional supplement composition to the human being.

9. The method of claim 8, wherein the unit dosage form consists of 181.38 mg L-arginine HCl; 170.93 mg L-pyroglutamic acid; 374.83 mg L-lysine HCl; 0.25 mg N-acetyl L-cysteine USP; 0.25 mg L-glutamine; and 0.125 mg Schizonepta (aerial parts) powder.

10. A method of improving sleep efficiency in a healthy human being in need thereof, comprising:
providing a serving of the nutritional supplement composition in unit dosage form, wherein the unit dosage form consists of:
3.44 mmol L-arginine;
5.30 mmol Oxo-proline;
8.21 mmol L-lysine;
6.13 µmol N-acetyl L-cysteine;
6.84 µmol L-glutamine; and
0.50 mg Schizonepta (aerial parts) powder; and
orally administering an effective amount of the nutritional supplement composition to the healthy human being.

11. The method of claim 10, wherein the unit dosage form consists of 725.50 mg L-arginine HCl; 683.70 mg L-pyroglutamic acid; 1499.30 mg L-lysine HCl; 1.00 mg N-acetyl L-cysteine USP; 1.00 mg L-glutamine; and 0.50 mg Schizonepta (aerial parts) powder.

12. The method of claim 10, where the effective amount of the nutritional supplement composition is 2.9 grams.

13. The method of claim 10, wherein the nutritional supplement composition is in powder, tablet, capsule, liquid or wafer form.

14. The method of claim 10, wherein orally administering the nutritional supplement composition to a healthy human being comprises orally administering the nutritional supplement composition to the human being from one to three times daily.

15. The method of claim 10, wherein orally administering the nutritional supplement composition to a healthy human being comprises orally administering the nutritional supplement composition to the human being once a week.

16. The method of claim 10, wherein orally administering the nutritional supplement composition to a healthy human being comprises orally administering the nutritional supplement composition to the human being on an empty stomach.

17. The method of claim 10, where the healthy human being is at least 30 years old.

* * * * *